United States Patent [19]

Danby et al.

[11] Patent Number: 4,759,264
[45] Date of Patent: Jul. 26, 1988

[54] PARENTERAL SOLUTION DIAPHRAGM PUMP

[75] Inventors: Hal C. Danby, Sudbury, England; Carl Ritson, San Jose, Calif.

[73] Assignee: Critikon, Inc., Tampa, Fla.

[21] Appl. No.: 799,235

[22] Filed: Nov. 18, 1985

[51] Int. Cl.$^4$ ............................ F01B 19/00; F16J 3/00
[52] U.S. Cl. ..................................... 92/99; 92/103 SD
[58] Field of Search .................. 92/89, 96, 98 R, 99, 92/103 SD, 103 R, 103 F, 103 M, 104, 91; 417/413

[56] References Cited

U.S. PATENT DOCUMENTS

| | | | |
|---|---|---|---|
| 988,472 | 4/1911 | Kinealy | 92/91 X |
| 2,261,265 | 11/1941 | Maass | 92/91 |
| 3,298,285 | 1/1967 | Webb | 92/98 R X |
| 3,385,168 | 5/1968 | Fineman et al. | 92/99 X |
| 4,231,287 | 11/1980 | Smiley | 92/98 R X |

FOREIGN PATENT DOCUMENTS

| | | | |
|---|---|---|---|
| 15180 | 9/1980 | European Pat. Off. | 417/413 |
| 901610 | 1/1954 | Fed. Rep. of Germany | 92/103 R |

*Primary Examiner*—Robert E. Garrett
*Assistant Examiner*—Mark A. Williamson
*Attorney, Agent, or Firm*—W. Brinton Yorks, Jr.

[57] ABSTRACT

A hinged plate diaphragm pump comprising a pumping chamber defined by an inflexible member and a flexible member opposed thereto. The flexible member has at least three inflexible plates with edges in a common plane. Each plate has at least two straight plate hinge edges, each plate hinge edge being adjacent to and aligned with a second plate hinge edge of an adjacent plate, the adjacent edges of each plate hinge edge and second plate hinge edge is attached together by a flexible hinge strip. Preferably, the plates comprise at least one array of plates positioned about an axial center of symmetry perpendicular to the common plane. The hinged plates can be hingedly connected to a surrounding support plate and an axially central plate positioned at the axis of symmetry.

7 Claims, 2 Drawing Sheets

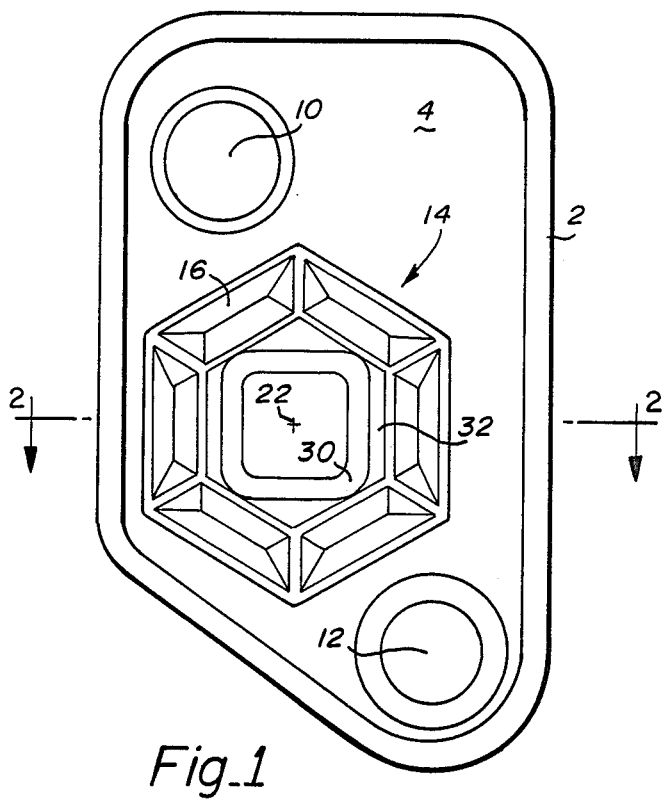
Fig_1
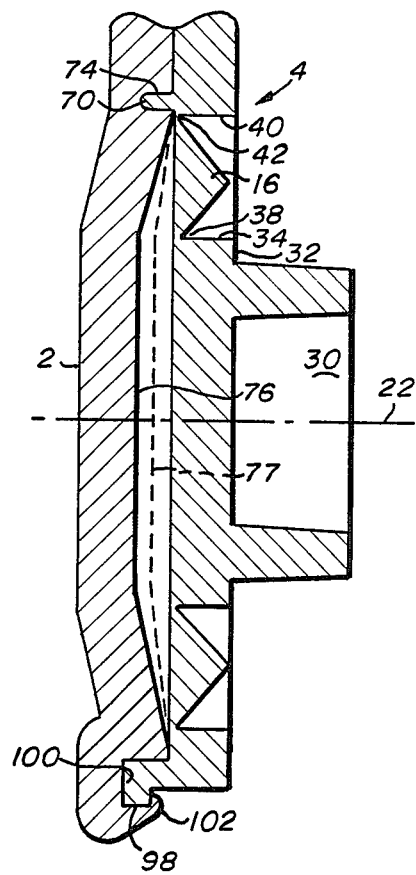
Fig_2
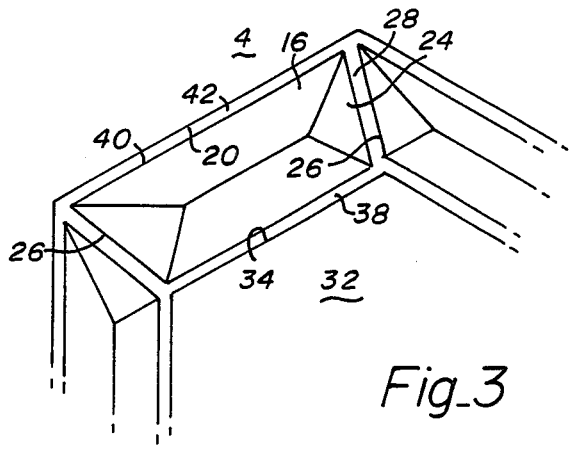
Fig_3

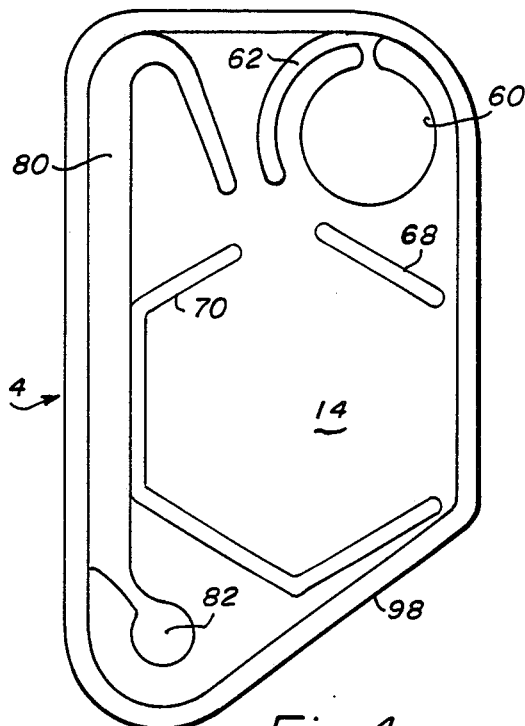
Fig_4
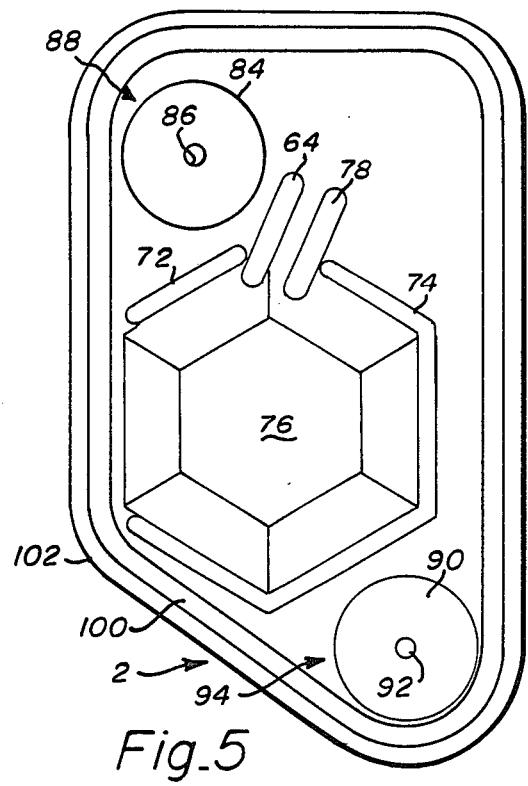
Fig_5
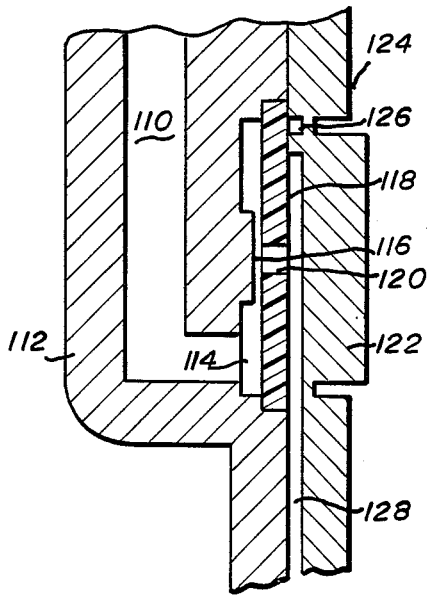
Fig_6
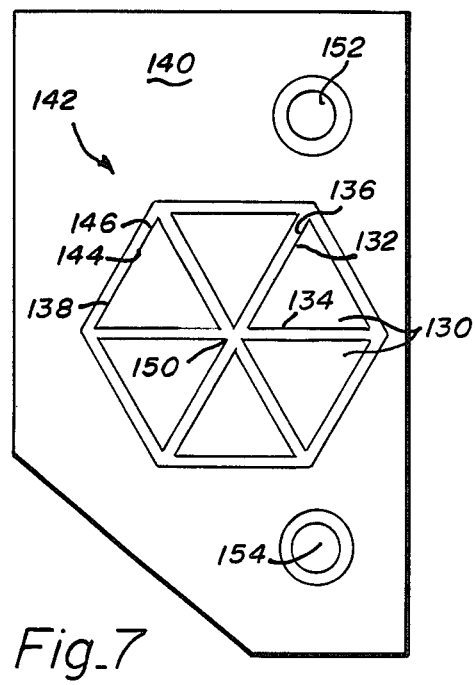
Fig_7

PARENTERAL SOLUTION DIAPHRAGM PUMP

FIELD OF THE INVENTION

This invention relates to a high accuracy diaphragm pump assembly which is useful for parenteral solution delivery systems. In particular, this invention relates to an inexpensive, disposable, high accuracy pump diaphragm system which is useful for pumping highly accurate amounts of liquids to a predetermined objective.

BACKGROUND OF THE INVENTION

The ability to pump predetermined volumes of liquids at a preset flow rate is important in many fields of industry and particularly in the medical field. Delivery of precise amounts of liquids at precise, preset flow rates is routinely required in hospital and clinical settings. The principal infusion systems in common use today use either gravity flow with flow control devices or pump delivery systems. This invention relates to improvements in pump delivery systems particularly useful as infusion pumps for metering preset volumes of parenteral solutions to patients at preset flow rates with light weight, low power, portable pumping units.

DESCRIPTION OF THE PRIOR ART

Three types of infusion metering pumps have been developed, peristaltic pumps such as are disclosed in U.S. Pat. No. 4,515,589, simple diaphragm pumps with inlet and outlet check valves such as are described by U.S. Pat. No. 2,954,738 and traditional piston pumps with either check valves or mechanically operated inlet and outlet valves. Isolation of the fluid passing through a pumping chamber from the mechanical pumping elements is usually achieved with diaphragms of flexible, elastic material, which can be a flexible tube as is described in combination with a diaphragm pump in U.S. Pat. No. 2,812,716 or in combination with pistons as described in U.S. Pat. No. 4,126,132 (piston rod 31 and diaphragm 73 in FIG. 1), U.S. Pat. No. 4,140,118 (piston 23 and diaphragm 19 in FIG. 2), U.S. Pat. No. 4,199,307 (actuator 67, flexible sleeve 111 and enclosed tubing 18 in FIGS. 2–4), U.S. Pat. No. 4,273,121 (piston 28 and diaphragm 26 in FIGS. 3 and 4), U.S. Pat. No. 4,276,004 (piston elements 10 and 13 and diaphragm 3 in FIG. 2), U.S. Pat. No. 4,290,346 (pump head 62 and flexible chamber walls 10 in FIGS. 2 and 4), U.S. Pat. Nos. 4,336,800 and 4,453,932 (piston 51 and flexible chamber wall and outlet valve actuator 13 in FIGS. 2 and 3), U.S. Pat. No. 4,468,222 (piston 161 and diaphragms 171 and 241 in FIGS. 5-7), and U.S. Pat. Nos. 4,453,931 and 4,457,753 (piston 53 and diaphragm 13 in FIG. 3).

Pump diaphragms with segmented pumping elements are described in U.S. Pat. Nos. 1,923,740 and 3,200,757. Valve diaphragm components are described in U.S. Pat. Nos. 1,034,323, 1,229,860, 3,661,060, 3,677,161, 4,078,580 and 4,208,031. A high pressure diaphragm with annular ring plate members flexibly connected with integral flexible connections are described in U.S. Pat. No. 4,231,287.

SUMMARY OF THE INVENTION

This invention is a hinged plate diaphragm pump comprising a pumping chamber defined by an inflexible member and a flexible member opposed thereto. The flexible member has at least three inflexible plates with edges in a common plane. Each plate has at least two straight plate hinge edges, each plate hinge edge being adjacent to and aligned with a second plate hinge edge of an adjacent plate, the adjacent edges of each plate hinge edge and second plate hinge edge is attached together by a flexible hinge strip. Preferably, the plates comprise at least one array of plates positioned about an axial center of symmetry perpendicular to the common plane, a drive connector being positioned at the axial center of symmetry. Most preferably, the array of plates comprise at least three identical plates having identical edges, the respective identical edges thereof being positioned equidistant from the axial center of symmetry.

In a preferred embodiment of this invention, the flexible member includes a support plate defining a hinged plate support opening with straight support plate edges, the distances between the ends of each support plate edge and the axial center of symmetry being substantially the same. In this embodiment, the plates include a first array of plates, each plate of which is hingedly connected to a support plate edge, each plate in the first array of plates having a straight support plate hinge edge positioned adjacent to and aligned with a support plate edge and hingedly connected to the support plate edge by a flexible hinge strip. In a preferred mode of this embodiment, the flexible member includes a center plate, the axial center of the center plate being at the axial center of symmetry, the center plate having straight center plate edges having the same length, and the plates include a second array of plates hingedly connected to the straight sides of the center plate, each plate in the second array of plates having a straight center plate hinge edge positioned adjacent to and aligned with a center plate edge and hingedly connected to the center plate edge by a flexible hinge strip.

BRIEF DESCRIPTION OF THE DRAWINGS

FIG. 1 is a front view of a pump assembly showing the segmented and hinged diaphragm according to this invention.

FIG. 2 is a fragmentary cross-sectional view taken along the line 2—2 in FIG. 1.

FIG. 3 is an enlarged fragmentary view of a diaphragm plate and hinge connections of the diaphragm plate shown in FIG. 1.

FIG. 4 is a back view of a front plate shown in FIG. 1.

FIG. 5 is a front view of the diaphragm back plate of the pump assembly shown in FIG. 1.

FIG. 6 is a fragmentary cross-sectional view of the inlet valve assembly according to this invention.

FIG. 7 is a front view of an alternate diaphragm plate according to this invention.

DETAILED DESCRIPTION OF THE INVENTION

The hinged plate diaphragm pump of this invention can accurately meter liquid at a preset rate and with a low power requirement because of the unique design of the hinged plate diaphragm.

FIG. 1 is a front view of the pump assembly showing one embodiment of the segmented and hinged diaphragm according to this invention; FIG. 2 is a fragmented cross-sectional view taken along the line 2—2 of FIG. 1; and FIG. 3 is a fragmentary view of a diaphragm and associated hinge elements. The diaphragm pump has two principal elements, an inflexible back plate 2 and a front plate with flexible elements 4. The front plate 4 is joined to the back plate 2 around its edges as is described in greater detail hereinafter. The pump has inlet and outlet check valves (not shown), the inlet check valve having an actuator 10 and the outlet check valve having an actuator 12.

The segmented and hinged diaphragm element 14 consists of a plurality of substantially rigid plates 16 hinged to each other and to the front plate 4. The front plate 4 defines an opening within which the hinged diaphragm 14 is hingedly mounted. The plurality of edges 20 of this opening are straight and have ends which are equally distant from the axis of symmetry 22 which extends perpendicular to the flexible plate 4.

Each of the plates 16 have at least two straight plate hinge edges 24 and 26. Each plate hinge edge is adjacent to and aligned with an opposed plate hinge edge of an adjacent plate. The adjacent plate hinge edges 24 and 26 are hinged to each other by a flexible hinge strip 28.

A pump drive connector 30 is positioned at the axial center 22. Preferably, the pump drive connector 30 is relatively inflexible and is connected to or integral with a central plate 32. The central plate 32 has straight central plate edges 34, the ends of which are all preferably equally distant from the axis of symmetry 22. The central plate edges 34 are positioned adjacent and aligned with opposing central plate hinge edges 36 of the plates 16. The central plate hinge edges 36 are joined to the central plate edges 34 by a flexible hinge strip 38.

The plates 16 have straight front plate hinge edges 40 aligned with opposing support plate edges 20 and hingedly connected thereto by flexible hinge strip 42.

A flexible plate member 14 moves toward the opposing wall 76 of the pump cavity from the initial position shown in solid lines to the extended position shown in the dotted lines 77. It then moves in the return direction to and optimally through the initial position to a retracted position (not shown). It then returns to the initial position, completing a full pumping cycle.

FIG. 4 is a back view of the front plate of FIG. 1 and FIG. 5 is a front view of the back plate, showing the engaging and opposing surfaces of the two plates before assembly. The front plate 4 is a single piece of molded plastic having channels and depressions which define the pumping chamber, inlet and outlet valve elements and the flow channels in the device, in addition to the diaphragm pump plates and hinges formed in the front surface thereof. The inlet valve element 60 communicates with the inlet flow channel 62. The inlet flow channel 62 communicates with the back side of the flexible diaphragm elements 14 by means of the flow channel 64 in the back plate (FIG. 5). The pump chamber is further defined by sealing extensions or ridges 68 and 70 in the front plate which engage with matching sealing channels 72 and 74 in the back plate 2. The sealing channels 72 and 74 provide a firm sealing wall defining the outer circumference of the cavity 76 of the pumping chamber, when engaging the ridges 68 and 70, maintain the desired liquid flow pattern from the pumping chamber as the diaphragm element 14 approaches the opposing cavity wall 76. This configuration also facilitates flushing of the air from all portions of the liquid flow path through the pump during priming, eliminating air pockets.

The liquid outlet channel from the pumping chamber is defined by the channel 78 in the back plate 2 which communicates with the channel 80 in the front plate 4. Channel 80 leads to the outlet valve element 82. The inlet valve components include a flexible sealing washer 84 with a fluid flow passageway 86 mounted in a corresponding inlet valve cavity 88 in the back plate 2. A schematic representation of the elements of the check valve is described in greater detail hereinafter in conjunction with FIG. 6. The outlet valve components include a flexible sealing washer 90 having a central fluid flow passageway 92 mounted in a corresponding outlet valve cavity 94 in the back plate 2.

The outer perimeter of the front plate 4 is a continuous sealing ridge 98 which is shaped to engage a corresponding channel 100 of the back plate 2.

Referring to FIG. 2, the ridge 98 engages the channel 100 in a firm, sealing engagement, and the extended edge 102 is swaged over the lip 104 to lock the engaging pieces in a fluid tight seal.

FIG. 6 is a fragmentary schematic view of a check valve assembly to show the relationship between the principle elements of the check valves 10 and 12. An inlet valve is shown, and the outlet valve has similar structural elements. The inlet fluid flow passageway 110 is present in the back plate 112, and leads to a check valve inlet cavity 114 with a stationary valve seat 116. The flexible valve element 118 is positioned opposing the valve seat 116 and has a fluid passageway opening 120 in the center thereof, aligned with the valve seat 116. The valve actuator element 122 is mounted in the front plate 124 by the hinge element 126. Movement of the valve actuator element 122 toward the valve seat 116 moves the valve element 118 into contact with the opposing valve seat 116, converting the valve elements into a check valve. Fluid passing through the passageway 120 moves through the passageway 128 toward the pumping cavity.

When the pump is in a filling stage, fluid flows through the passageway 110, into the cavity 114, opening 120 and passageway 128. When the pump is in the compression stage, the fluid pressure in the passageway 128 increases, and the flexible member 118 is pressed by fluid pressure against the valve seat 116, closing the opening 120 to fluid flow. Thus reverse fluid motion is prevented during the pressure stage of the pumping operation.

FIG. 7 shows an alternate configuration of hinged diaphragm plates. In this embodiment, a plurality of equilateral triangle plates 130 each have a pair of straight sides 132 and 134 of equal length, joined to adjacent plates by flexible hinge strips 136. The base 138 of each triangle is a straight line. The plate 140 to which these plates are mounted defines a cavity 142 having straight edges 144 corresponding in length and configuration with the bases 138 of the assembled plates. The bases 138 are connected to the opposing, aligned edges 144 by hinge strips 146. The diaphragm drive is connected to the axial center 150 of the array of triangular plates. Inlet and outlet valve elements 152 and 154 can also be formed in the plate 140.

In the embodiments illustrated in the drawings, a total of six plates are assembled in a symmetrical array around the axial center. It will be readily apparent that the number of plates can be selected as desired, a minimum of three plates being required for operation in the intended manner. The flexible hinge elements are distorted by both flexure and stretching during the movement of the diaphragm element, and as the number of segments are reduced, greater energy is expended to effect flexure. Stretch distortion of the hinge increases toward the center of the diaphragm, and this distortion is increased by reducing the number of plates. Increasing the number of segments increases the flexible hinge area and reduces the stretching required for diaphragm movement, both reducing energy requirements. Increasing the hinge width and reducing the thickness of the hinge also increases hinge flexibility and elasticity, further reducing energy requirements. However, increasing the number of plates, increasing the relative hinge area and reducing the hinge thickness increases non-linear pumping errors.

An important achievement of the flexible plate diaphragm is the reduction of pumping volume variations which are a function of liquid pressure. Liquid pressure rising in the pumping chamber during a positive pumping stroke and falling during the filling stroke tends to stretch the diaphragm, increasing or decreasing the volume of the pumping chamber, and introducing a non-linear variable in the liquid volume output or input per stroke. The volume displaced during a positive stroke is thus less than would be calculated by simple displacement, and the volume filled during a filling stroke is less than would be calculated by a simple displacement calculation. Because the degree of distortion is a function of the varying pumping chamber pressures, which is in turn, a function of the pumping rate and outlet valve and line back-pressure, this type of distortion cannot be adequately compensated by microcomputer control adjustments and seriously impairs pumping accuracy.

This effect is very pronounced with the flexible diaphragm pumps known prior to this invention. Piston pumps, while avoiding this problem, use more power and require a more complex construction to prevent leakage from the pumping chamber around the piston.

With the plate diaphragm construction of this invention, however, the increased pressure in the pumping chamber does not significantly flex the plate elements, and a more linear relationship between displacement and delivered volume is achieved. With the hinged plate diaphragm of this invention, diaphragm flexure is resisted by the relatively inflexible plates. Only the hinge areas will flex. Thus, the areas subject to flexure are minimized, consistent with the designed power and pressure restraints of a portable, battery operated unit, for example. The diaphragm of FIG. 1, having a central plate and six equal segments, represents a studied compromise of these factors, and is believed to represent a preferred configuration for use with the pump configuration for parenteral solution delivery shown in the drawings.

The plate bearing the flexible plate components and the individual plate element of the diaphragm are preferably relatively rigid to achieve maximum accuracy. This can be achieved by bonding rigid plate elements to a flexible sheet. For example, a relatively rigid polymer can be bonded to a flexible, elastic polymer, combining the rigidity and flexibility desired. In a preferred embodiment of this invention, elements of the front plate bearing the hinged plate diaphragm are formed from a single, homogeneous sheet of plastic. Rigidity is achieved by thickness and flexibility by thinness. Polyolefin plastics such as polyethylene can be used for this construction, for example. In this embodiment, the rigid plates and the flexible hinges are integral parts of a single unit. Corresponding check valve elements can be similarly formed in same sheet of plastic. The back plate can be made of a suitable rigid plastic such as ABS polymer.

We claim:

1. A diaphragm pump comprising a pumping chamber defined by an inflexible member having a first chamber surface and a flexible member having a second chamber surface opposed thereto, the flexible member comprising a central inflexible plate surrounded by at least three inflexible peripheral plates with substantially flat chamber surfaces and edges in a common plane, each plate having at least two straight plate hinge edges, each straight plate hinge edge being adjacent to and opposing a straight plate hinge of an adjacent plate, the opposing edges of each straight plate hinge edge and opposing straight plate hinge edge being attached together by a thin flexible hinge strip which separates said opposing straight edges by a uniform distance along said opposing edges.

2. The diaphragm pump of claim 1 wherein the plates comprise at least one array of plates positioned about an axial center of symmetry perpendicular to the common plane, a drive connector being positioned at the axial center of symmetry.

3. The diaphragm pump of claim 1 wherein the peripheral plates comprise at least three identical plates having identical edges, the respective identical edges thereof being positioned equally distant from the axial center of symmetry.

4. The diaphragm pump of claim 3 wherein the peripheral plates comprise six plates.

5. The diaphragm pump of claim 3, wherein the center plate exhibits straight center plate edges having the same length, and the peripheral plates comprise an array of trapezoidal plates hingedly connected to the straight sides of the center plate, each plate in the array of plates having a straight center plate hinge edge positioned adjacent to and aligned with a center plate edge and hingedly connected to the center plate edge by a flexible hinge edge.

6. The diaphragm pump of claim 5 wherein the center plate is a hexagon and the array of plates comprises six identical plates having a trapezoidal configuration.

7. The diaphragm pump of claim 3 wherein the flexible member includes a support plate defining a hinged plate support opening with straight support plate edges, the distances between the ends of each support plate edge and the axial center of symmetry being substantially the same, and the plates include a first array of plates, each plate of which is hingedly connected to a support plate edge, each plate in the first array of plates having a straight support plate hinge edge positioned adjacent to and aligned with a support plate edge and hingedly connected to the support plate edge by a flexible hinge strip.

* * * * *